United States Patent [19]

Breu et al.

[11] Patent Number: 5,856,484
[45] Date of Patent: Jan. 5, 1999

[54] SULFONYLAMINOPYRIMIDINE CARBOXYLIC ACID DERIVATIVES HAVING ENDOTHELIN INHIBITING ACTIVITY

[75] Inventors: Volker Breu, D-Schliengen, Germany; Kaspar Burri, Binningen, Switzerland; Jean-Marie Cassal, Mulhouse, France; Martine Clozel, St. Louis, France; Georges Hirth, Huningue, France; Bernd-Michael Löffler, Oberrimsingen, Germany; Marcel Müller, Frenkendorf, Switzerland; Werner Neidhart, Bartenheim, France; Henri Ramuz, Birsfelden, Switzerland

[73] Assignee: Hoffmann-La Roche Inc., Nutley, N.J.

[21] Appl. No.: 726,712

[22] Filed: Oct. 7, 1996

[30] Foreign Application Priority Data

Oct. 12, 1995 [CH] Switzerland ............... 2893/95

[51] Int. Cl.⁶ ............... C07D 239/47; C07D 403/12; C07D 403/14
[52] U.S. Cl. ............... 544/319; 544/295; 544/296; 544/238; 544/122; 544/123; 544/82
[58] Field of Search ............... 544/319, 295, 544/296, 238, 122, 123, 82

[56] References Cited

U.S. PATENT DOCUMENTS 5,270,313 12/1993 Burri et al. ............... 514/252
5,292,740 3/1994 Burri et al. ............... 514/256
5,420,129 5/1995 Breu et al. ............... 514/252
5,541,186 7/1996 Breu et al. ............... 514/256

FOREIGN PATENT DOCUMENTS

A-0 658 548  6/1995  European Pat. Off. .
A-0 768 304  10/1996  European Pat. Off. .

OTHER PUBLICATIONS

Abstract Accession Number 97–214767/20 Incomplete Citation.

Life Sci, 44:1429 (1989).

Adachi et al., BBRC 180:1265–1272.

*Primary Examiner*—John M. Ford
*Attorney, Agent, or Firm*—George W. Johnston; Dennis P. Tramaloni; Bruce A. Pokras

[57] ABSTRACT

Compounds of formula I:

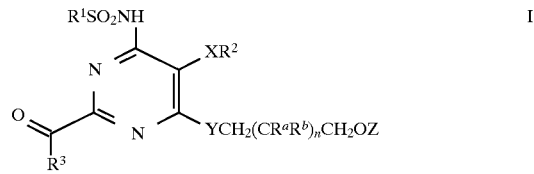

are disclosed. The compounds inhibit the binding of endothelin to its receptors.

94 Claims, No Drawings

SULFONYLAMINOPYRIMIDINE CARBOXYLIC ACID DERIVATIVES HAVING ENDOTHELIN INHIBITING ACTIVITY

SUMMARY OF THE INVENTION

The present invention is concerned with novel sulfonylaminopyrimidine carboxylic acid derivatives, pharmaceutical compositions containing those compounds, and methods of treating a host suffering from a disease in which the binding of endothelin to its receptors is a causative factor in the disease symtoms or damage.

In particular, the invention is concerned with novel compounds of formula I:

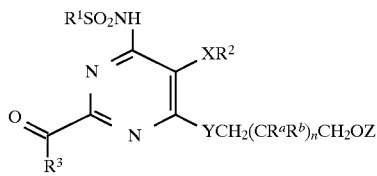

wherein
- $R^1$ is phenyl, substituted phenyl or heterocyclyl;
- $R^2$ is phenyl or substituted phenyl;
- $R^3$ is hydroxy, lower-alkoxy or a residue $—NR^4R^5$;
- $R^4$ is hydrogen or a residue $—R^6$ and
- $R^5$ is hydrogen or a residue $—(CH_2)_mR^6$ or
- $R^4$ and $R^5$ together with the N atom to which they are attached are an N heterocyclic residue;
- $R^6$ is phenyl, substituted phenyl, cycloalkyl, heterocyclyl, lower-alkyl, hydroxy-lower-alkyl, amino-lower-alkyl, carboxy-lower-alkyl or lower-alkoxycarbonyl-lower-alkyl;
- $R^a$ is hydrogen, lower-alkyl or hydroxy;
- $R^b$ is hydrogen or lower-alkyl;
- X is oxygen or sulphur;
- Y is oxygen or sulphur;
- Z is hydrogen, lower-alkyl, aryl, aryl-lower-alkyl, heterocyclyl or heterocyclyl-lower-alkyl;
- m is 0, 1 or 2; and
- n is 0, 1 or 2;

and pharmaceutically acceptable salts thereof.

DETAILED DESCRIPTION OF THE INVENTION

Phenyl residues can be substituted by lower-alkyl, lower-alkoxy, methylenedioxy, ethylenedioxy, lower-alkanoyl, hydroxy, amino, mono- or di-lower-alkylamino and/or halogen. The term "lower" used herein denotes groups with 1–7 C atoms, preferably 1–4 C atoms. Alkyl and alkoxy groups as well as alkyl groups as components of alkanoyl groups can be straight-chain or branched. Methyl, ethyl, propyl, isopropyl, butyl, sec.butyl and tert.butyl are examples of such alkyl groups. Halogen denotes fluorine, chlorine, bromine and iodine, with chlorine being preferred.

Examples of heterocyclyl residues are mono- or bicyclic 5- and 6-membered heterocyclic residues containing oxygen, nitrogen or sulphur as the hetero atom(s), such as 2- and 3-furyl, pyrimidinyl, 2-, 3- and 4-pyridyl, 2-tetrazolyl-4-pyridyl, 1,2- and 1,4-diazinyl, morpholino, 2- and 3-thienyl, isoxazolyl, oxazolyl, thiazolyl, imidazolyl, pyrrolyl and tetrazolyl, which can be substituted e.g. by lower-alkyl, lower-alkanoyl, hydroxy, lower-alkanoyloxy, lower-alkoxy, lower-alkoxycarbonyl, formyl, amino, mono- or di-lower-alkylamino or halogen. N-Heterocyclic residues formed with $R^4$ and $R^5$ are preferably monocyclic 6-membered heterocyclyl residues which can contain a further oxygen or nitrogen atom, such as morpholino, piperidino, piperazino and $N^4$-lower-alkylpiperazino.

Preferred residues $R^1$ are phenyl, which is substituted by lower-alkyl or lower-alkoxy, and monocyclic heterocyclyl residues which contain a nitrogen atom, such as pyridyl, especially 2-pyridyl, and which can be substituted, preferably monosubstituted, by lower-alkyl. The especially preferred residues $R^1$ are p-tert-butyl phenyl, p-methoxy phenyl, 5-methyl-2-pyridyl and 5-isopropyl-2-pyridyl.

Preferred residues $R^2$ are phenyl, which is substituted by lower-alkoxy or halogen. The especially preferred residues $R^2$ are m-methoxy phenyl, o-chloro-m-methoxy phenyl and o-methoxy phenyl, with m-methoxy phenyl being the most preferred.

Preferred residues $R^3$ are hydroxy and $—NR^4R^5$, with the preferred $R^4$ being hydrogen and the preferred $R^5$ being phenyl, pyridyl, morpholino or tetrazolyl. n is preferably 0 or 1. When n is 1, $R^a$ is preferably hydroxy and $R^b$ is preferably hydrogen. X and Y are preferably oxygen. Z is preferably hydrogen or pyrimidinyl, especially hydrogen.

The compounds of formula I and their salts are endothelin receptor inhibitors. They can therefore be used for the treatment of disorders which are known to be associated with endothelin activities, especially circulatory disorders such as hypertension, ischemia, vasospasms and angina pectoris.

The compounds of formula I and their salts can be manufactured in accordance with the invention by converting the residue A in a compound of formula II

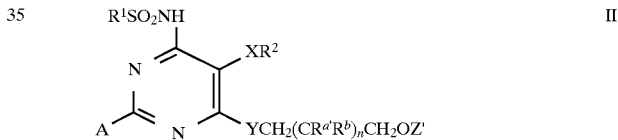

wherein A represents a residue convertible into a carboxyl group and $R^1$, $R^2$, X, Y, $R^b$ and n have the significance given above, Z' is Z as described above or a hydroxy protecting group, and $R^{a'}$ is $R^a$ as described above or protected hydroxy, into a carboxyl group and optionally converting the hydroxy group $R^3$ in a thus-obtained compound of formula I in which $R^3$ is hydroxy into a lower-alkoxy group or a group $—NR^4R^5$ or into a pharmaceutically usable salt.

Preferred residues A are the formyl group and the furan-2-yl residue. These residues can be converted into a carboxy group in a manner known per se by treatment with oxidizing agents, with groups which are present in the starting material of formula II and which are not inert towards the oxidizing agent which is employed, such as hydroxy groups, preferably being protected. A suitable oxidizing agent for the oxidation of a formyl group to a carboxyl group is, e.g., potassium permanganate. The oxidation can be carried out in a suitable inert solvent such as benzene in the presence of a crown ether at room temperature. The hydroxy group explicitly indicated in formula I as well as hydroxy groups present as $R^a$ or in $R^1$, or when Z is hydrogen, can be protected by any conventional means. One conventional means of protecting the hydroxy group is to convert the hydroxy group to an ester such as the acetate or to a ketal, e.g., to the acetonide. A furan-2-yl group can be oxidized to the carboxyl group by treatment with periodate, e.g., Na periodate in the presence of ruthenium trichloride in a two-phase system containing $CCl_4$, acetonitrile and water.

The compounds of formula II are novel and are likewise an object of the invention. Compounds of formula II in which A is a formyl residue can be prepared from corresponding methyl compounds (see European Patent Publication EP-A 0526708) by oxidation, e.g., with selenium dioxide (see European Patent Publication EP-A 0601386). Compounds of formula II in which A is the furan-2-yl residue and Y is oxygen or sulphur can be prepared starting from compounds of the formula

by condensation with 2-furanylamidine to give a 2-furan-2-yl-(5-$XR^2$)pyrimidine-4,6-diol, replacement of the OH groups by Cl by treatment with $POCl_3$, reaction of the 4,6-dichloropyrimidine derivative with a sulphonamide salt of the formula $R^1SO_2NHM$ and thereafter with a compound of the formula:

wherein Y' represents oxygen or sulphur, M represents a cation, e.g., an alkali cation such as $Na^+$ or $K^+$, and X represents a protecting group and wherein a hydroxy group which may be represented by $R^a$ is present in protected form.

The thus-formed carboxy group can be converted in a manner known per se into a lower-alkyl ester ($R^3$=lower alkoxy) or an amide ($R^3$=—$NR^4R^5$) or into a pharmaceutically acceptable salt. Any pharmaceutically acceptable salt may be used in accordance with the present invention. Examples of pharmaceutically acceptable salts are alkali salts such as the Na salt and the K salt and alkaline earth salts such as the Ca salt and the Mg salt.

The compounds of formula I exhibit a selective inhibitory activity on endothelin receptors A and B ($ET_A$ and $ET_B$), which can be demonstrated using the test procedures described hereinafter:

I, Inhibition of endothelin binding to recombinant $ET_A$ receptors

A cDNA coding for human ETA receptors of human placenta was cloned (M. Adachi, Y.-Y. Yang, Y. Furuichi and C-Miyamoto, BBRC 180, 1265–1272) and expressed in the baculovirus-insect cell system. Baculovirus-infected insect cells from a 23 I fermentor are centrifuged off (3000×g, 15 minutes, 4° C.) 60 hours after the infection, re-suspended in Tris buffer (5 mM, pH 7.4, 1 mM $MgCl_2$) and again centrifuged. After a further re-suspension and centrifugation the cells are suspended in 800 ml of the same buffer and freeze-dried at −120° C. The cells disintegrate when the suspension in this hypotonic buffer mixture is thawed. After a repeated freeze-drying/thawing cycle the suspension is homogenized and centrifuged (25000 x g, 15 minutes, 4° C.). After suspension in Tris buffer (75 mM, pH 7.4, 25 mM $MgCl_2$, 250 mM sucrose) 1 ml aliquots (protein content about 3.5 mg/ml) are stored at −85° C.

For the binding assay, the freeze-dried membrane preparations are thawed and, after centrifugation at 20° C. and 25000 g for 10 minutes, re-suspended in assay buffer (50 mM Tris buffer pH 7.4, containing 25 mM $MnCl_2$, 1 mM EDTA and 0.5% bovine serum albumin). 100 $\mu$l of this membrane suspension containing 5 $\mu$g of protein are incubated with 50 $\mu$l of $^{125}$I-endothelin (specific activity 2200 Ci/mMol) in assay buffer (25000 cpm, final concentration 20 $\mu$M) and 100 $\mu$l of assay buffer containing varying concentrations of test compound. The incubation is carried out at 20° C. for 2 hours or at 4° C. for 24 hours. The separation of free and membrane-bound radioligands is carried out by filtration over a glass fibre filter.

II. Inhibition of endothelin binding to human placenta membranes ($ET_B$ receptors) (see Life Sci 44:1429 (1989))

Human placenta is homogenized in 5 mM Tris buffer, pH 7.4, which contains 1 mM $MgCl_2$ and 250 mM sucrose. The homogenizate is centrifuged at 4° C. and 3000 g for 15 minutes, the supernatant containing the plasma membrane fraction is centrifuged at 72000 g for 30 minutes and the precipitate is washed with 75 mM Tris buffer, pH 7.4, which contains 25 mM $MgCl_2$. Thereafter, precipitate obtained from in each case 10 g of original tissue is suspended in 1 ml of 75 mM Tris buffer, pH 7.4, containing 25 mM $MgCl_2$ and 250 mM sucrose and freeze-dried at −20° C. in 1 ml aliquots.

For the binding assay, the freeze-dried membrane preparations are thawed and, after centrifugation at 20° C. and 25000 g for 10 minutes, re-suspended in assay buffer (50 mM Tris buffer, pH 7.4, containing 25 mM $MnCl_2$, 1 mM EDTA and 0.5% bovine serum albumin). 100 $\mu$l of this membrane suspension containing 35 $\mu$g of protein are incubated with 50 $\mu$l of $^{125}$I-endotheline (specific activity 2200 (Ci/mMol) in assay buffer (25000 cpm, final concentration 20 pM) and 100 $\mu$l of assay buffer containing varying concentrations of test compound. The incubation is carried out at 20° C. for 2 hours or at 4° C. for 24 hours. The separation of free and membrane-bound radioligands is carried out by filtration over a glass fibre filter.

The inibitory activity on $ET_A$ and $ET_B$ receptors of compounds of formula I determined in these test procedures is given in Table 1 as the $IC_{50}$, i.e. as the concentration [$\mu$M] which is required to inhibit 50% of the specific binding of $^{125}$I-endothelin.

TABLE 1

| Compound of Example | $ET_A$ $IC_{50}$ [$\mu$M] | $ET_B$ $IC_{50}$ [$\mu$M] |
| --- | --- | --- |
| 1 | 73 | 0.08 |
| 2 | 1.83 | 0062 |
| 5 | 16.4 | 0.29 |
| 6 | 38 | 063 |
| 7 | 18.2 | 0.3 |
| 8 | 13 | 0.06 |
| 9 | 21.4 | 0.086 |
| 10 | 13 | 0.14 |

On the basis of their capability of inhibiting endothelin binding, the compounds of the invention can be used as medicament for the treatment of disorders which are known to be associated with the binding of endothelin to its receptors. Examples of such disorders are high blood pressure, especially pulmonary high pressure, as well as sub-arachnoid haemorrhage. Further indications for which the compounds in accordance with the invention can be used are coronary disorders, cardiac insufficiency, renal and myocardial ischemia, renal insufficiency, cerebral ischemia, cerbral infact, migraine and Raynaud's syndrome.

The compounds in accordance with the invention can also be used in atherosclerosis, the prevention of restenosis after balloon-induced vascular dilation, inflammations, gastric and duodenal ulcers, ulcers cruris, gram-negative sepsis, shock, glomerulonephritis, renal colic, glaucoma, asthma, in dialysis and in the therapy and prophylaxis of diabetic complications and complications in the administration of cyclosporin, as well as other disorders associated with endothelin activities.

The compounds of formula I can be administered orally, rectally, parentally, e.g., intravenously, intramuscularly, subcutaneously, intrathecally or transdermally; or sublingually or as ophthalmological preparations, or as an aerosol. Capsules, tablets, suspensions or solutions for oral administration, suppositories, injection solutions, eye drops, salves or spray solutions are examples of administration forms.

Intravenous, intramuscular or oral administration is a preferred form of use. The dosages in which the compounds of formula I are administered in effective amounts depending on the nature of the specific active ingredient, the age and the requirements of the patient and the mode of administration. Dosages may be determined by any conventional means, e.g., by dose-limiting clinical trials. Thus, the invention further comprises a method of treating a host suffering from a disease in which endothielin binding to its receptors is a causative factor in the disease symptoms or damage by administering an amount of a compound of the invention sufficient to inhibit endothelin binding to its receptors so that said symptoms or said damage is reduced. In general, dosages of about 0.1–100 mg/kg body weight per day come into consideration.

The invention further comprises pharmaceutical compositions which contain a pharmaceutically effective amount of a compound of the invention and a pharmaceutically acceptable carrier. Tablets or granulates, e.g., can contain a series of binders, fillers, carriers or diluents. Liquid compositions can be , for example, in the form of a sterile water-miscible solution. Capsules can contain a filler or thickener in addition to the active ingredient. Furthermore, flavour-improving additives as well as substances usually used as preserving, stabilizing, moisture-retaining and emulsifying agents as well as salts for varying the osmotic pressure, buffers and other additives can also be present.

The previously mentioned carrier materials and diluents can comprise any conventional pharmaceutically acceptable organic or inorganic substances, e.g., water, gelatine, lactose, starch, magnesium stearate, talc, gum arabic, polyalkylene glycols and the like.

Oral unit dosage forms, such as tablets and capsules, preferably contain from 10 mg to 100 mg of a compound of the invention.

The following Examples illustrate the invention in more detail.

Example 1 a) 25 g of resorcinol monomethyl ether and 37 g of dimethyl chloromalonate were added to a solution of 4.6 g of sodium in 150 ml of methanol. The reaction mixture was stirred at 45° C. under argon for 4 hours, filtered and partitioned between toluene/water. The organic phase was dried with sodium sulphate and the solvent was distilled off. 40.7 g of methyl (RS)-(3-methoxy-phenoxy)-acetoacetate were obtained as an oil, MS: (M+H)$^+$ 255.

b) 17 g of acetamidine hydrochloride and 40 g of methyl (RS)-(3-methoxy-phenoxy)-acetoacetate were added to a sodium methylate solution prepared from 450 ml of methanol and 11.3 g of sodium. The reaction mixture was stirred at 20° C. for 2 hours, concentrated and partitioned between toluene/water. The aqueous phase was adjusted to pH 4 with 2N HCl and stirred at 0° C. for 16 hours. The precipitate was filtered off, washed with water and ether and dried. 25.7 g of 6-hydroxy-5-(3-methoxy-phenoxy)-2-methyl-3H-pyrimidin-4-one were obtained as a white solid, MS: (M+H)$^+$ 249.

c) 24.5 ml of Hunig base and 23.6 ml of POCl$_3$ were added to a solution of 11.9 g of 6-hydroxy-5-(3-methoxy-phenoxy)-2-methyl-3H-pyrimidin-4-one in 150 ml of dioxan. The reaction mixture was stirred at 120° C. for 16 hours and thereafter the excess reagent and the dioxan were distilled off. The residue was concentrated twice with toluene and partitioned between chloroform-water. The organic phase was washed with NaHCO$_3$ and with water, dried and concentrated. The residue was purified over silica gel with hexane and dichloromethane. 9.1 g of 4,6-dichloro-5-(3-methoxy-phenoxy)-2-methyl-pyrimidine were obtained as a yellowish oil, MS: (M+H)$^+$ 286.

d) 9 g of 4,6-dichloro-5-(3-methoxy-phenoxy)-2-methyl-pyrimidine and 17 g of K p-tert.-butylsulphonamide in 35 ml of dry dimethyl sulphoxide were heated to 120° C. under argon for 3 hours. Thereafter, DMSO was distilled off, the residue was partitioned between ethyl acetate and 1N hydrochloric acid and the organic phase was washed neutral. The organic phase was dried, the solvent was evaporated and the residue was treated with 35 ml of methanol. 11.1 g of p-tert.butyl-N-[6-chloro-5-(m-methoxyphenoxy)-2-methyl-4-pyrimidinyl-benzenesulphonamide, m.p. 170° C., were obtained.

e) 11 g of p-tert.butyl-N-[6-chloro-5-(m-methoxyphenoxy)-2-methyl-4-pyrimidinyl-benzenesulphonamide were added to a sodium glycolate solution prepared from 35 g of ethylene glycol and 1.66 g of sodium. The reaction mixture was stirred at 95° C. under argon for 16 hours, thereafter treated with 100 ml of 1N hydrochloric acid and 50 ml of water and extracted twice with 100 ml of ethyl acetate. The organic phase was washed with water, dried and evaporated. The residue was crystallized from dichloromethane-isopropyl ether. There were obtained 8.8 g of p-tert.butyl-N-[6-(2-hydroxyethoxy)-2-methyl-5-(m-methoxyphenoxy)-4-pyrimidinyl]benzenesulphonamide, m.p. 139° C., MS: (M+H)$^+$ 488.

f) 0.2 g of dimethylaminopyridine and 3.9 ml of acetic anhydride were added to a solution of 1 g of p-tert.butyl-N-[6-(2-hydroxyethoxy)-2-methyl-5-(m-methoxyphenoxy)-4-pyrimidinyl]benzenesulphonamide in 40 ml of dichloromethane. The reaction mixture was stirred at 20° C. for 3 hours and adjusted to pH 7 with a sat. NaHCO$_3$ solution. The organic phase was washed with water, dried and evaporated. The residue was purified over silica gel with chloroform. 1.1 g of 2-[6-acetyl-(4-tert.butyl-phenylsulphonyl)-amino]-5-(3-methoxy-phenoxy)-2-methyl-pyrimidin-4-yloxy]-ethyl acetate were obtained as a foam, MS: (M+H)$^+$ 572.

g) 0.2 g of 2-[6-acetyl-(4-tert.butyl-phenylsulphonyl)-amino]-5-(3-methoxy-phenoxy)-2-methyl-pyrimidin-4-yloxy]-ethyl acetate and 0.6 g of selenium dioxide were stirred in 10 ml of dioxan at 140° C. in an autoclave for 50 hours. The reaction mixture was filtered and the filtrate was concentrated. The residue was partitioned between ethyl acetate and water. The organic phase was dried, the solvent was evaporated and the residue was purified over silica gel with chloroform-methanol 95:5. 0.27 g of 2-[6-(4-tert.butyl-phenylsulphonylamino)-2-formyl-5-(3-methoxy-phenoxy)-pyrimidin-4-yloxy]-ethyl acetate was obtained as a foam, MS: (M+H)$^+$ 544.

h) 0.27 g of 2-[6-(4-tert.butyl-phenylsulphonylamino)-2-formyl-5-(3-methoxy-phenoxy)-pyrimidin-4-yloxy]-ethyl acetate and 0.19 g of dicyclohexyl-18-crown-6 in 15 ml of benzene were stirred with 0.078 g of potassium permanganate at 2000 for 16 hours. The reaction mixture was partitioned between toluene and water. The organic phase was dried and evaporated, and the residue was purified over silica gel with chloroform-methanol. 0.09 g of 4-(2-acetoxy-ethoxy)-6-(4-tert.butyl-phenylsulphonylamino)-5-(3-methoxy-phenoxy)-pyrimidine-2-carboxylic acid was obtained as a foam, MS: (M–H)$^-$ 558.

i) 0.09 g of 4-(2-acetoxy-ethoxy)-6-(4-tert.butyl-phenyl-sulphonylamino)-5-(3-methoxy-phenoxy)-pyrimidine-2-carboxylic acid in 4 ml of methanol and 1.5 ml of water was stirred with 0.05 g of sodium carbonate at 20° C. for 2 hours. The methanol was evaporated and the residue was partitioned between chloroform and aqueous 1N hydrochloric acid. The organic phase was dried and evaporated. The residue was purified over silica gel with chloroform-methanol-water, 60:35:5. There was obtained 0.034 g of 6-(4-tert.butyl-phenylsulphonylamino)-4-(2-hydroxy-ethoxy)-5-(3-methoxy-phenoxy)-pyrimidine-2-carboxylic acid, MS: (M–H)$^-$ 515.9.

Example 2

4-(4-tert.Butyl-phenylsulphonylamino)-5-(2-chloro-5-methoxy-phenoxy)-6-(2-hydroxy-ethoxy)-pyrimidine-2-carboxylic acid, MS: (M–H)$^-$ 550.2, was prepared from 2-chloro-5-methoxy-phenol in analogy to Example 1 via the following intermediates:

a) Methyl (RS)-(2-chloro-5-methoxy-phenoxy)-acetoacetate,
b) 6-hydroxy-5-(2-chloro-5-methoxy-phenoxy)-2-methyl-3H-pyrimidin-4-one,
c) 4,6-dichloro-5-(2-chloro-5-methoxy-phenoxy)-2-methyl-pyrimidine,
d) p-tert.butyl-N-[6-chloro-5-(2-chloro-5-methoxyphenoxy)-2-methyl-4-pyrimidinyl]benzenesulphonamide,
e) p tert.butyl-N-[6-(2-hydroxyethoxy)-2-methyl-5-(2-chloro-5-methoxyphenoxy)-4-pyrimidinyl]benzenesulphonamide,
f) 2-[6-(4-tert.butyl-phenylsulphonylamino)-5-(2-chloro-5-methoxy-phenoxy)-2-methyl-pyrimidin-4-yloxy]-ethyl acetate,
g) 2-[6-(4-tert.butyl-phenylsulphonylamino)-5-(2-chloro-5-methoxy-phenoxy)-2-formyl-pyrimidin-4-yloxy]-ethyl acetate,
h) 4-(2-acetoxy-ethoxy)-6-(4-tert.butyl-phenylsulphonylamino)-5-(2-chloro-5-methoxy-phenoxy)-pyrimidine-2-carboxylic acid.

Example 3

4-(2-Hydroxy-ethoxy)-5-(3-methoxy-phenoxy)-6-(4-methoxy-phenylsulphonylamino)-pyrimidin-2-carboxylic acid, MS: (M–H)$^-$ 490.3, was prepared from 4,6-dichloro-5-(3-methoxy-phenoxy)-2-methyl-pyrimidine in analogy to Example 1 via the following intermediates:

a) N-[6-Chloro-5-(3-methoxy-phenoxy)-2-methyl-pyrimidin-4-yl]-4-methoxy-benzenesulphonamide,
b) N-[6-(2-hydroxy-ethoxy)-5-(3-methoxy-phenoxy)-2-methyl-pyrimidin-4-yl]-4-methoxy-benzenesulphonamide,
c) 2-[6-(4-methoxy-phenylsulphonylamino)-5-(m-methoxy-phenoxy)-2-methyl-pyrimidin-4-yloxy]-ethyl acetate,
d) 2-[6-(4-methoxy-phenylsulphonylamino)-5-(m-methoxy-phenoxy)-2-formyl-pyrimidin-4-yloxy]-ethyl acetate,
e) 4-(2-acetoxy-ethoxy)-6-(4-methoxy-phenylsulphonylamino)-5-(m-methoxy-phenoxy)-pyrimidine-2-carboxylic acid.

Example 4 a) In analogy to Example 1b, from 34 g of ethyl (RS)-(3-methoxy-phenoxy)-acetoacetate and 23 g of 2-furanylamidine there were obtained 15.6 g of 2-(furan-2-yl)-5-(3-methoxy-phenoxy)-pyrimidine-4,6-diol as a foam, MS: (M+H)$^+$ 300.

b) In analogy to Example 1c), from 15.5 g of 2-(furan-2-yl)-5-(3-methoxy-phenoxy)-pyrimidine-4,6-diol and 43 ml of POCl$_3$ there were obtained 15.9 g of 4,6-dichloro-2-(furan-2-yl)-5-(3-methoxy-phenoxy)-pyrimidine, m.p. 106° C., MS: (M+H)$^+$ 338.

c) In analogy to Example 1d), from 1 g of 4,6-dichloro-2-(furan-2-yl)-5-(3-methoxy-phenoxy)-pyrimidine and 1.5 g of K p-tert.butylsulphonamide there were obtained 1.34 g of 4-tert.-butyl-N-[6-chloro-2-(furan-2-yl)-5-(3-methoxy-phenoxy)-pyrimidin-4-yl]-benzenesulphonamide, MS: (M–H)$^-$ 513.

d) In analogy to Example 1e), from 0.3 g 4-tert.butyl-N-[6-chloro-2-(furan-2-yl)-5-(3-methoxy-phenoxy)-pyrimidin-4-yl]-benzenesulphonamide and 12 ml of DL-isopropylidene-glycerol there was obtained 0.25 g of (RS)-4-tert.butyl-N-[6-(2,2-dimethyl-[1,3]dioxolan-4-ylmethoxy)-2-(furan-2-yl)-5-(3-methoxy-phenoxy)-pyrimidin-4-yl]-benzenesulphonamide, m.p. 135° C., MS: (M–H)$^-$ 608.

e) A solution of 0.7 g of sodium periodate and 0.015 g of ruthenium chloride in 10 ml of water was added to a solution of 0.25 g of (RS)-4-tert.butyl-N-[6-(2,2-dimethyl-[1,3]dioxolan-4-ylmethoxy)-2-(furan-2-yl)-5-(3-methoxy-phenoxy)-pyrimidin-4-yl]-benzenesulphonamide in 3.6 ml of CCl$_4$ and 3.6 ml of acetonitrile. The reaction mixture was stirred at 20° C. for 1 hour and extracted with methylene chloride. The organic phase was dried and evaporated. The residue was purified over silica gel with chloroform. There was obtained 0.04 g of (RS)-4-(4-tert.butyl-phenylsulphonylamino-6-(2,2-dimethyl-[1,3]dioxolan-4-ylmethoxy)-5-(3-methoxy-phenoxy)-pyrimidine-2-carboxylic acid, MS: (M–H)$^-$ 586.

f) A solution of 0.033 g of (RS)-4-(4-tert.butyl-phenyl-sulphonylamino-6-(2,2-dimethyl-[1,3]dioxolan-4-ylmethoxy)-5-(3-methoxy-phenoxy)-pyrimidine-2-carboxylic acid in 2 ml of dioxan was treated with 1.3 ml of 1N HCl and heated to 90° C. for 30 minutes. After evaporation the residue was chromatographed over silica gel with chloroform-methanol-water 60:35:5 as the eluent and yielded 0.007 g of (RS)-6-(4-tert.butyl-phenylsulphonylamino)-4-(2,3-dihydroxy-propoxy)-5-(3-methoxy-phenoxy)-pyrimidine-2-carboxylic acid as a foam, MS: (M–H)$^-$ 546.

Example 5

In analogy to Example 4e), from 2-[6-(4-tert.butyl-phenylsulphonylamino)-2-(furan-2-yl)-5-(2-methoxy-phenoxy)-pyrimidin-4-yloxy]-ethyl acetate there was obtained 4-(2-acetoxy-ethoxy)-6-(4-tert.butyl-phenylsulphonylamino)-5-(2-methoxy-phenoxy)-pyrimidine-2-carboxylic acid, MS: (M–H)$^-$ 558, and therefrom in analogy to Example 1i) there was obtained 6-(4-tert.butyl-phenylsulphonylamino)-4-(2-hydroxy-ethoxy)-5-(2-methoxy-phenoxy)-pyrimidine-2-carboxylic acid, MS: (M–H)$^-$ 516.4.

Example 6

0.2 ml of Hunig base, 0.052 g of bis-(2-oxo-3-oxazolidinyl)-phosphinic acid chloride and 0.01 ml of aniline were added to a solution of 0.053 g of 6-(4-tert.butyl-phenylsulphonylamino)-4-(2-hydroxy-ethoxy)-5-(3- methoxy-phenoxy)-pyrimidine-2-carboxylic acid in 5 ml of acetonitrile. After 3 hours the reaction mixture was evaporated and partitioned between ethyl acetate and water. The organic phase was dried and evaporated, and the residue purified over silica gel with chloroform. There was obtained 0.032 g of 6-(4-tert.butyl-phenylsulphonylamino)-4-(2-hydroxy-ethoxy)-5-(3-methoxy-phenoxy)-pyrimidine-2-carboxylic acid phenylamide, m.p. 143° C., MS: (M–H)⁻ 591.

Example 7

4-(2-Hydroxy-ethoxy)-5-(3-methoxy-phenoxy)-6-(4-methoxy-phenylsulphonylamino)-pyrimidine-2-carboxylic acid phenylamide, MS: (M+H)⁺ 567, was obtained in analogy to Example 6.

Example 8

6-(4-tert.Butyl-phenylsulphonylamino)-5-(2-methoxy-phenoxy)-4-(2-hydroxy-ethoxy)-pyrimidine-2-carboxylic acid phenylamide, MS: (M–H)⁻ 591, was obtained in analogy to Example 6.

Example 9

4-(4-tert.Butyl-phenylsulphonylamino)-5-(2-chloro-5-methoxy-phenoxy)-6-(2-hydroxy-ethoxy)-pyrimidine-2-carboxylic acid phenylamide, MS: (M+H)⁺ 628, was obtained in analogy to Example 6.

Example 10

4-(4-tert.Butyl-phenylsulphonylamino)-6-(2-hydroxy-ethoxy)-5-(3-methoxy-phenoxy)-pyrimidine-2-carboxylic acid (1 H-tetrazol-5-yl)-amide, MS: (M–H)⁻ 583, was obtained in analogy to Example 6.

Example 11

In analogy to Example 4, paragraph c), d), e), from 4,6-dichloro-2-(furan-2-yl)-5-(3-methoxy-phenoxy)-pyrimidine there were obtained:
 a) 5-isopropyl-pyridine-2-sulphonic acid [6-chloro-2-(furan-2-yl)-5-(3-methoxy-phenoxy)-pyrimidin-4-yl]-amide
 b) 5-isopropyl-pyridine-2-sulphonic acid [2-(furan-2-yl)-6-(2-hydroxy-ethoxy)-5-(3-methoxy-phenoxy)-pyrimidin-4-yl]-amide
 c) 2-[6-[acetyl-(5-isopropyl-pyridin-2-ylsulphonyl)-amino]-2-(furan-2-yl)-5-(3-methoxy-phenoxy)-pyrimidin-4-yloxy]-ethyl acetate
 d) 4-(2-acetoxy-ethoxy)-6-(5-isopropyl-pyridin-2-ylsulphonyl)-amino]-5-(3-methoxy-phenoxy)-pyrimidine-2-carboxylic acid
and therefrom in analogy to Example 1 there was obtained 4-(2-hydroxy-ethoxy)-6-(5-isopropyl-pyridin-2-ylsulphonylamino)-5-(3-methoxy-phenoxy)-pyrimidine-2-carboxylic acid, MS: (M–H)⁻ 503.

Example 12

In analogy to Example 4, paragraph c), d), e) from 4,6-dichloro-2-(furan-2-yl)-5-(3-methoxy-phenoxy)-pyrimidine there were obtained:
 a) 5-Methyl-pyridine-2-sulphonic acid [6-chloro-2-(furan-2-yl)-5-(3-methoxy-phenoxy)-pyrimidin-4-yl]-amide
 b) 5-methyl-pyridine-2-sulphonic acid [2-(furan-2-yl)-6-(2-hydroxy-ethoxy)-5-(3-methoxy-phenoxy)-pyrimidin-4-yl]-amide
 c) 2-[2-(furan-2-yl)-5-(3-methoxy-phenoxy)-6-(5-methyl-pyridin-2-ylsulphonylamino)-pyrimidin-4-yloxy]-ethyl acetate
 d) 4-(2-acetoxy-ethoxy)-6-(5-methyl-pyridin-2-ylsulphonyl)-amino]-5-(3-methoxy-phenoxy)-pyrimidin-2-carboxylic acid
and therefrom in analogy to Example 1 there was obtained 4-(2-hydroxy-ethoxy)-6-(5-isopropyl-pyridin-2-ylsulphonylamino)-5-(3-methoxy-phenoxy)-pyrimidine-2-carboxylic acid, MS: (M–H)⁻ 475.

Example 13

4-(2-Hydroxyethoxy)-5-(3-methoxyphenoxy)-6-(5-methyl-pyridin-2-ylsulphonylamino)pyrimidine-2-carboxylic acid (1 H-tetrazol-5-yl)amide can be obtained in analogy to Example 6.

Example 14

(R,S)-6-(2,3-Dihydroxy-propoxy)-5-(3-methoxyphenoxy)-4-(5-methylpyridin-2-yl-sulphonylamino)-pyrimidine-2-carboxylic acid can be obtained in analogy to Example 4.

Example 15

6-(4-tert.Butylphenylsulphonylamino)-4-(2,3-dihydroxy-propoxy)-5-(3-methoxyphenoxy)pyrimidine-2-carboxylic acid (1 H-tetrazol-5-yl)amide can be obtained in analogy to Example 6.

Example 16

4-tert-Butyl-N-[6-(2-hydroxy-ethoxy)-5-(3-methoxy-phenoxy)-2-(morpholin-4-ylcarboxyl)-pyrimidin-4-yl]-benzenesulphonamide, MS: (M–H)⁻ 585, was obtained in analogy to Example 6.

Example 17

4-(4-tert-Butyl-phenylsulphonylamino)-6-(2-hydroxy-ethoxy)-5-(3-methoxy-phenoxy)-pyrimidine-2-carboxylic acid pyridin-3-ylamide, MS: (M–H)⁻ 592, was obtained in analogy to Example 6.

Example 18

4-(4-tert-Butyl-phenylsulphonylamino)-6-(2-hydroxy-ethoxy)-5-(3-methoxy-phenoxy)-pyrimidine-2-carboxylic acid (3-hydroxy-phenyl)-amide, MS: (M–H)⁻ 607, was obtained in analogy to Example 6.

Example 19

4-(4-tert-Butyl-phenylsulphonylamino)-6-(2-hydroxy-ethoxy)-5-(3-methoxy-phenoxy)-pyrimidine-2-carboxylic acid (2-hydroxymethyl-phenyl)-amide, MS: (M+H)⁺ 623, was obtained in analogy to Example 6.

Example 20

4-(4-tert-Butyl-phenylsulphonylamino)-6-(2-hydroxyethoxy)-5-(3-methoxy-phenoxy)-pyrimidine-2-carboxylic acid (3-hydroxymethyl-phenyl)-amide, MS (M–H)⁻ 621, was obtained in analogy to Example 6.

Example 21

(RS)-4-(4-tert-Butyl-phenylsulphonylamino)-6-(2,3-dihydroxy-propoxy)-5-(3-methoxy-phenoxy)-pyrimidine-2-carboxylic acid pyridin-3-ylamide, MS: (M–H)⁻ 622, was obtained in analogy to Example 6.

Example 22

(RS)-4-(4-tert-Butyl-phenylsulphonylamino)-6-(2,3-dihydroxy-propoxy)-5-(3-methoxy-phenoxy)-pyrimidine-2-carboxylic acid (3-hydroxy-phenyl)-amide, MS: (M−H)⁻ 637, was obtained in analogy to Example 6.

Example 23

0.2 g of 6-(4-tert-butyl-phenylsulphonylamino)-4-(2-hydroxy-ethoxy)-5-(3-methoxy-phenoxy)-pyrimidine-2-carboxylic acid in 5 ml of dimethylacetamide was stirred at 20° C. for 3 hours with 0.04 g of sodium hydride and 0.07 g of 2-chloropyrimidine and the mixture was neutralized with saturated NH₄Cl solution. The reaction mixture was washed with ethyl acetate. The aqueous phase was adjusted to pH 2 with 1N HCl and extracted with chloroform. The organic phase was dried, the solvent was evaporated and the residue was purified over silica gel with chloroform-methanol-water 60:35:5. There was obtained 0.16 g of 4-(4-tert-butyl-phenylsulphonylamino)-5-(3-methoxy-phenoxy)-6-(2-pyrimidin-2-yloxy-ethoxy)-pyrimidine-2-carboxylic acid, MS: (M+H)⁺ 596.

Example A

Tablets containing the following ingredients can be produced in a conventional manner:

| Ingredients | Per tablet |
| --- | --- |
| Compound of formula I | 10.0–100.0 mg |
| Lactose | 125.0 mg |
| Corn starch | 75.0 mg |
| Talc | 4.0 mg |
| Magnesium stearate | 1.0 mg |

Example B

Capsules containing the following ingredients can be produced in a conventional manner:

| Ingredients | Per capsule |
| --- | --- |
| Compound of formula I | 25.0 mg |
| Lactose | 150.0 mg |
| Corn starch | 20.0 mg |
| Talc | 5.0 mg |

Example C

Injection solutions can have the following composition:

| | |
| --- | --- |
| Compound of formula I | 3.0 mg |
| Gelatine | 150.0 mg |
| Phenol | 4.7 mg |
| Water for injection solutions | ad 1.0 ml |

Example D 500 mg of compound of formula I are suspended in 3.5 ml of Myglyol 812 and 0.08 g of benzyl alcohol. This suspension is filled into a container having a dosage valve. 5.0 g of Freon 12 are filled into the container under pressure through the valve. The Freon is dissolved in the Myglyol-benzyl alcohol mixture by shaking. This spray container contains about 100 single doses, which can be applied individually.

We claim:

1. A compound of the formula:

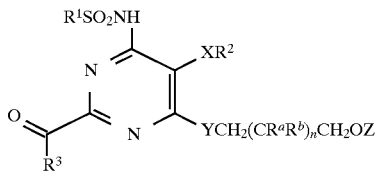

wherein $R^1$ is phenyl; a substituted phenyl substituted by a chemical group selected from the group consisting of lower alkyl, lower alkoxy, methylenedioxy, ethylenedioxy, lower-alkanoyl, hydroxy, amino, mono-lower-alkylamino, di-lower-alkylamino or halogen; or heterocyclyl selected from the group consisting of 2-furyl, 3-furyl, pyrimidinyl, 2-pyridyl, 3-pyridyl, 4-pyridyl, 2-tetrazolyl-4-pyridyl, 1,2-diazinyl, 1,4-diazinyl, morpholino, 2-thienyl, 3-thienyl, isoxazolyl, oxazolyl, thiazolyl, imidazolyl, pyrrolyl and tetrazolyl;

$R^2$ is phenyl or a substituted phenyl substituted by a chemical group selected from the group consisting of lower alkyl, lower alkoxy, methylenedioxy, ethylenedioxy, lower-alkanoyl, hydroxy, amino, mono-lower-alkylamino, di-lower-alkylamino and halogen;

$R^3$ is hydroxy, lower alkoxy or —$NR^4R^5$;

$R^4$ is hydrogen or —$R^6$ and $R^5$ is hydrogen or —$(CH_2)mR^6$ or $R^4$ and $R^5$ together are an N-heterocyclylic chosen from the group consisting of morpholino, piperidino, piperazino and $N^4$-lower-alkylpiperazino;

$R^6$ is phenyl; cycloalkyl; lower-alkyl; hydroxy lower alkyl; amino-lower-alkyl; carboxy-lower-alkyl; lower-alkoxycarbonyl- lower-alkyl; a substituted phenyl substituted by a chemical group selected from the group consisting of lower alkyl, lower alkoxy, methylenedioxy, ethylenedioxy, lower-alkanoyl, hydroxy, amino, mono-lower-alkylamino, di-lower-alkylamino or halogen; or heterocyclyl chosen from the group consisting of 2-furyl, 3-furyl, pyrimidinyl, 2-pyridyl, 3-pyridyl, 4-pyridyl, 2-tetrazolyl-4-pyridyl, 1,2-diazinyl, 1,4-diazinyl, morpholino, 2-thienyl, 3-thienyl, isoxazolyl, oxazolyl, thiazolyl, imidazolyl, pyrrolyl and tetrazolyl;

$R^a$ is hydrogen, lower-alkyl or hydroxy;

$R^b$ is hydrogen or lower alkyl;

X is oxygen or sulfur;

Y is oxygen or sulfur;

Z is hydrogen; lower-alkyl; aryl; aryl-lower-alkyl; heterocyclyl selected from the group consisting of 2-furyl, 3-furyl, pyrimidinyl, 2-pyridyl, 3-pyridyl, 4-pyridyl, 2-tetrazolyl-4-pyridyl, 1,2-diazinyl, 1,4-diazinyl, morpholino, 2-thienyl, 3-thienyl, isoxazolyl, oxazolyl, thiazolyl, imidazolyl, pyrrolyl and tetrazolyl; or heterocyclyl selected from the group consisting of 2-furyl, 3-furyl, pyrimidinyl, 2-pyridyl, 3-pyridyl, 4-pyridyl, 2-tetrazolyl-4-pyridyl, 1,2-diazinyl, 1,4-diazinyl, morpholino, 2-thienyl. 3-thienyl, isoxazolyl, oxazolyl, thiazolyl, imidazolyl, pyrrolyl and tetrazolyl, wherein the heterocyclyl is substituted with lower-alkyl;

m is 0, 1, or 2; and, n is 0, 1, or 2;

and pharmaceutically acceptable salts thereof.

2. The compound of claim 1 wherein X and Y are both oxygen.

3. The compound of claim 2 wherein Z is hydrogen.

4. The compound of claim 3 wherein $R^1$ is phenyl which is para-substituted by lower alkyl or lower alkoxy.

5. The compound of claim 4 wherein $R^1$ is phenyl which is para-substituted by lower alkyl.

6. The compound of claim 5 wherein $R^3$ is hydroxy or —$NHR^5$ in which $R^5$ is phenyl, pyridyl or tetrazolyl, which $R^5$ group may be unsubstituted or substituted.

7. The compound of claim 6 wherein $R^3$ is —$NHR^5$ in which $R^5$ is phenyl which is unsubstituted or substituted by hydroxy or lower alkyl-hydroxy.

8. The compound of claim 7 wherein $R^2$ is phenyl which is substituted by lower alkoxy or chloro.

9. The compound of claim 8 wherein $R^2$ is phenyl which is monosubstituted by lower alkoxy.

10. The compound of claim 9 wherein $R^1$ is p-tert-butyl phenyl, $R^2$ is m-methoxy phenyl, and $R^5$ is phenyl.

11. The compound of claim 10 wherein said compound is 6-(4-tert.butyl-phenylsulphonylamino)-4-(2-hydroxy-ethoxy)-5-(3-methoxy-phenoxy)-pyrimidine-2-carboxylic acid phenylamide.

12. The compound of claim 9 wherein $R^1$ is p-tert-butyl-phenyl, $R^2$ is m-methoxy phenyl, and $R^5$ is substituted phenyl.

13. The compound of claim 12 wherein $R^5$ is phenyl monosubstituted by hydroxyl or —$CH_2OH$.

14. The compound of claim 13 wherein said compound is (RS)-4-(4-tert-Butyl-phenylsulphonylamino)-6-(2,3-dihydroxy-propoxy)-5-(3-methoxy-phenoxy)-pyrimidine-2-carboxylic acid (3-hydroxy-phenyl)-amide.

15. The compound of claim 13 wherein said compound is 4-(4-tert-Butyl-phenylsulphonylamino)-6-(2-hydroxy-ethoxy)-5-(3-methoxy-phenoxy)-pyrimidine-2-carboxylic acid (3-hydroxy-phenyl)-amide.

16. The compound of claim 13 wherein said compound is 4-(4-tert-Butyl-phenylsulphonylamino)-6-(2-hydroxyethoxy)-5-(3-methoxy-phenoxy)-pyrimidine-2-carboxylic acid (3-hydroxymethyl-phenyl)-amide.

17. The compound of claim 13 wherein said compound is 4-(4-tert-Butyl-phenylsulphonylamino)-6-(2-hydroxy-ethoxy)-5-(3-methoxy-phenoxy)-pyrimidine-2-carboxylic acid (2-hydroxymethyl-phenyl)-amide.

18. The compound of claim 9 wherein $R^1$ is p-tert-butyl phenyl, $R^2$ is o-methoxy phenyl, and $R^5$ is phenyl.

19. The compound of claim 18 wherein said compound is 6-(4-tert.Butyl-phenylsulphonylamino)-5-(2-methoxy-phenoxy)-4-(2-hydroxy-ethoxy)-pyrimidine-2-carboxylic acid phenylamide.

20. The compound of claim 8 wherein $R^2$ is phenyl which is substituted by lower alkoxy and chloro.

21. The compound of claim 20 wherein $R^3$ is —$NHR^5$ in which $R^5$ is phenyl or phenyl substituted by hydroxy or lower alkyl-hydroxy.

22. The compound of claim 21 wherein $R^1$ is p-tert-butyl phenyl, $R^2$ is o-chloro-m-methoxy phenyl, and $R^5$ is phenyl.

23. The compound of claim 22 wherein said compound is 4-(4-tert.Butyl-phenylsulphonylamino)-5-(2-chloro-5-methoxy-phenoxy)-6-(2-hydroxy-ethoxy)-pyrimidine-2-carboxylic acid phenylamide.

24. The compound of claim 6 wherein $R^3$ is hydroxy.

25. The compound of claim 24 wherein $R^2$ is phenyl which is substituted by lower alkoxy or chloro.

26. The compound of claim 25 wherein $R^2$ is phenyl which is monosubstituted by lower alkoxy.

27. The compound of claim 26 wherein $R^2$ is m-methoxy phenyl.

28. The compound of claim 27 wherein $R^1$ is p-tert-butyl phenyl.

29. The compound of claim 28 wherein said compound is 6-(4-tert.butyl-phenylsulphonylamino)-4-(2-hydroxy-ethoxy)-5-(3-methoxy-phenoxy)-pyrimidine-2-carboxylic acid.

30. The compound of claim 28 wherein said compound is (RS)-6-(4-tert.butyl-phenylsulphonylamino)-4-(2,3-dihydroxy-propoxy)-5-(3-methoxy-phenoxy)-pyrimidine-2-carboxylic acid.

31. The compound of claim 26 wherein $R^1$ is p-tert-butyl phenyl and $R^2$ is o-methoxy phenyl.

32. The compound of claim 31 wherein said compound is 6-(4-tert.butyl-phenylsulphonylamino)-4-(2-hydroxy-ethoxy)-5-(2-methoxy-phenoxy)-pyrimidine-2-carboxylic acid.

33. The compound of claim 25 wherein $R^2$ is phenyl which is substituted by lower alkoxy and chloro.

34. The compound of claim 33 wherein $R^1$ is p-tert-butyl phenyl and $R^2$ is o-chloro-m-methoxy phenyl.

35. The compound of claim 34 wherein said compound is 4-(4-tert.Butyl-phenylsulphonylamino)-5-(2-chloro-5-methoxy-phenoxy)-6-(2-hydroxy-ethoxy)-pyrimidine-2-carboxylic acid.

36. The compound of claim 6 wherein $R^3$ is —$NHR^5$ in which $R^5$ is pyridyl which is unsubstituted or substituted.

37. The compound of claim 36 wherein $R^2$ is phenyl which is substituted by lower alkoxy or chloro.

38. The compound of claim 37 wherein $R^2$ is phenyl which is monosubstituted by lower alkoxy.

39. The compound of claim 38 wherein $R^1$ is p-tert-butyl phenyl, $R^2$ is m-methoxy phenyl, and $R^5$ is pyridyl.

40. The compound of claim 39 wherein said compound is 4-(4-tert-Butyl-phenylsulphonylamino)-6-(2-hydroxy-ethoxy)-5-(3-methoxy-phenoxy)-pyrimidine-2-carboxylic acid pyridin-3-ylamide.

41. The compound of claim 39 wherein said compound is (RS)-4-(4-tert-Butyl-phenylsulphonylamino)-6-(2,3-dihydroxy-propoxy)-5-(3-methoxy-phenoxy)-pyrimidine-2-carboxylic acid pyridin-3-ylamide.

42. The compound of claim 38 wherein $R^1$ is p-tert-butyl phenyl.

43. The compound of claim 42 wherein $R^2$ is m-methoxy phenyl and $R^5$ is tetrazolyl.

44. The compound of claim 43 wherein said compound is 4-(4-tert.Butyl-phenylsulphonylamino)-6-(2-hydroxy-ethoxy)-5-(3-methoxy-phenoxy)-pyrimidine-2-carboxylic acid (1H-tetrazol-5-yl)-amide.

45. The compound of claim 43 wherein said compound is 6-(4-tert.Butylphenylsulphonylamino)-4-(2,3-dihydroxypropoxy)-5-(3-methoxyphenoxy)pyrimidine-2-carboxylic acid (1H-tetrazol-5-yl)amide.

46. The compound of claim 5 wherein $R^3$ is a group —$NR^4R^5$ in which $R^4$ and $R^5$ together with the N atom to which they are attached are an N-heterocyclic ring.

47. The compound of claim 46 wherein said N-heterocyclic ring is selected from the group consisting of morpholino, piperidino, piperazino and $N^4$-lower-alkylpiperazino.

48. The compound of claim 47 wherein $R^2$ is phenyl which is substituted by lower alkoxy or chloro.

49. The compound of claim 48 wherein $R^2$ is phenyl which is monosubstituted by lower alkoxy.

50. The compound of claim 49 wherein $R^1$ is p-tert-butyl phenyl, $R^2$ is m-methoxy phenyl, and $R^4$ and $R^5$ together with the N atom to which they are attached are morpholino.

51. The compound of claim 50 wherein said compound is 4-tert-Butyl-N-[6-(2-hydroxy-ethoxy)-5-(3-methoxyphenoxy)-2-(morpholin-4-ylcarboxyl)-pyrimidin-4-yl]-benzenesulphonamide.

52. The compound of claim 4 wherein $R^1$ is phenyl para-substituted by lower alkoxy.

53. The compound of claim 52 wherein $R^3$ is hydroxy or —$NHR^5$ in which $R^5$ is phenyl, pyridyl or tetrazolyl, which $R^5$ group may be unsubstituted or substituted.

54. The compound of claim 53 wherein $R^3$ is —$NHR^5$ in which $R^5$ is phenyl which is unsubstituted or substituted by hydroxy or lower alkyl-hydroxy.

55. The compound of claim 54 wherein $R^2$ is phenyl which is substituted by lower alkoxy or chloro.

56. The compound of claim 55 wherein $R^2$ is phenyl which is monosubstituted by lower alkoxy.

57. The compound of claim 56 wherein $R^1$ is p-methoxy phenyl, $R^2$ is m-methoxy phenyl, and $R^5$ is phenyl.

58. The compound of claim 57 wherein said compound is 4-(2-Hydroxy-ethoxy)-5-(3-methoxy-phenoxy)-6-(4-methoxy-phenylsulphonylamino)-pyrimidine-2-carboxylic acid phenylamide.

59. The compound of claim 53 wherein $R^3$ is hydroxy.

60. The compound of claim 59 wherein $R^2$ is phenyl which is substituted by lower alkoxy or chloro.

61. The compound of claim 55 wherein $R^2$ is phenyl which is monosubstituted by lower alkoxy.

62. The compound of claim 61 wherein $R^1$ is p-methoxy phenyl and $R^2$ is m-methoxy phenyl.

63. The compound of claim 62 wherein said compound is 4-(2-Hydroxy-ethoxy)-5-(3-methoxy-phenoxy)-6-(4-methoxy-phenylsulphonylamino)-pyrimidin-2-carboxylic acid.

64. The compound of claim 3 wherein $R^1$ is pyridyl which is unsubstituted or substituted.

65. The compound of claim 64 wherein $R^1$ is 5-lower alkyl-2-pyridyl.

66. The compound of claim 65 wherein $R^3$ is hydroxy or —$NHR^5$ in which $R^5$ is phenyl, pyridyl or tetrazolyl, which $R^5$ group may be unsubstituted or substituted.

67. The compound of claim 66 wherein $R^3$ is —$NHR^5$ in which $R^5$ is tetrazolyl.

68. The compound of claim 67 wherein $R^2$ is phenyl which is substituted by lower alkoxy or chloro.

69. The compound of claim 68 wherein $R^2$ is phenyl which is monosubstituted by lower alkoxy.

70. The compound of claim 69 wherein $R^1$ is 5-methyl-2-pyridyl and $R^2$ is m-methoxy phenyl.

71. The compound of claim 70 wherein said compound is 4-(2-Hydroxyethoxy)-5-(3-methoxyphenoxy)-6-(5-methyl-pyridin-2-ylsulphonylamino)pyrimidine-2-carboxylic acid (1 H-tetrazol-5-yl)amide.

72. The compound of claim 66 wherein $R^3$ is hydroxy.

73. The compound of claim 72 wherein $R^2$ is phenyl which is substituted by lower alkoxy or chloro.

74. The compound of claim 73 wherein $R^2$ is phenyl which is monosubstituted by lower alkoxy.

75. The compound of claim 74 wherein $R^2$ is m-methoxy phenyl.

76. The compound of claim 75 wherein $R^1$ is 5-methyl-2-pyridyl.

77. The compound of claim 76 wherein said compound is 4-(2-hydroxy-ethoxy)-6-(5-isopropyl-pyridin-2-ylsulphonylamino)-5-(3-methoxy-phenoxy)-pyrimidine-2-carboxylic acid.

78. The compound of claim 76 wherein said compound is (R,S)-6-(2,3-Dihydroxy-propoxy)-5-(3-methoxyphenoxy)-4-(5-methylpyridin-2-yl-sulphonylamino)-pyrimidine-2-carboxylic acid.

79. The compound of claim 75 wherein $R^1$ is 5-isopropyl-2-pyridyl.

80. The compound of claim 79 wherein said compound is 4-(2-hydroxy-ethoxy)-6-(5-isopropyl-pyridin-2-ylsulphonylamino)-5-(3-methoxy-phenoxy)-pyrimidine-2-carboxylic acid.

81. The compound of claim 2 wherein Z is lower-alkyl, aryl, aryl-lower-alkyl, heterocyclyl or heterocyclyl-lower-alkyl.

82. The compound of claim 81 wherein Z is heterocyclyl.

83. The compound of claim 82 wherein Z is 2-pyrimidinyl.

84. The compound of claim 83 wherein $R^3$ is hydroxy or —$NHR^5$ in which $R^5$ is phenyl, pyridyl or tetrazolyl, which $R^5$ group may be unsubstituted or substituted.

85. The compound of claim 84 wherein $R^3$ is —$NHR^5$ in which $R^5$ is phenyl which is unsubstituted or substituted by hydroxy or lower alkyl-hydroxy.

86. The compound of claim 85 wherein $R^2$ is phenyl which is substituted by lower alkoxy or chloro.

87. The compound of claim 86 wherein $R^2$ is phenyl which is monosubstituted by lower alkoxy.

88. The compound of claim 87 wherein $R^1$ is p-tert-butyl phenyl, $R^2$ is m-methoxy phenyl, and $R^5$ is phenyl.

89. The compound of claim 84 wherein $R^3$ is hydroxy.

90. The compound of claim 89 wherein $R^2$ is phenyl which is substituted by lower alkoxy or chloro.

91. The compound of claim 90 wherein $R^2$ is phenyl which is monosubstituted by lower alkoxy.

92. The compound of claim 91 wherein $R^1$ is p-tert-butyl phenyl and $R^2$ is m-methoxy phenyl.

93. The compound of claim 92 wherein said compound is 4-(4-tert-butyl-phenylsulphonylamino)-5-(3-methoxy-phenoxy)-6-(2-pyrimidin-2-yloxy-ethoxy)-pyrimidine-2-carboxylic acid.

94. A compound of the formula:

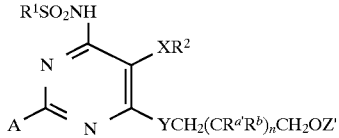

wherein A is formyl or furan-2-yl;

$R^1$ is phenyl; a substituted phenyl substituted by a chemical group selected from the group consisting of lower alkyl, lower alkoxy, methylenedioxy, ethylenedioxy, lower-alkanoyl, hydroxy, amino, mono-lower-alkylamino, di-lower-alkylamino and halogen; or heterocyclyl selected from the group consisting of 2-furyl, 3-furyl, pyrimidinyl, 2-pyridyl, 3-pyridyl, 4-pyridyl, 2-tetrazolyl-4-pyridyl, 1,2-diazinyl, 1,4-diazinyl, morpholino, 2-thienyl, 3-thienyl, isoxazolyl, oxazolyl, thiazolyl, imidazolyl, pyrrolyl and tetrazolyl;

$R^2$ is phenyl or a substituted phenyl substituted by a chemical group selected from the group consisting of lower alkyl, lower alkoxy, methylenedioxy, ethylenedioxy, lower-alkanoyl, hydroxy, amino, mono-lower-alkylamino, di-lower-alkylamino and halogen;

$R^{a'}$ is a protected hydroxy, hydrogen, lower-alkyl or hydroxy;

$R^b$ is hydrogen or lower alkyl;

X is oxygen or sulfur;

Y is oxygen or sulfur;

n is 0, 1, or 2;

Z' is a hydroxy protecting group; hydrogen; lower-alkyl; aryl; aryl-lower-alkyl; heterocyclyl selected from the group consisting of 2-furyl, 3-furyl, pyrimidinyl, 2-pyridyl, 3-pyridyl, 4-pyridyl, 2-tetrazolyl-4-pyridyl, 1,2-diazinyl, 1,4-diazinyl, morpholino, 2-thienyl, 3-thienyl, isoxazolyl, oxazolyl, thiazolyl, imidazolyl, pyrrolyl and tetrazolyl; or heterocyclyl selected from the group consisting of 2-furyl, 3-furyl, pyrimidinyl, 2-pyridyl, 3-pridyl, 4-pyridyl, 2-tetrazolyl-4-pyridyl, 1,2-diazinyl, 1,4-diazinyl, morpholino, 2-thienyl, 3-thienyl, isoxazolyl, oxazolyl, thiazolyl, imidazolyl, pyrrolyl and tetrazolyl, wherein the heterocyclyl is substituted with lower-alkyl.

* * * * *